United States Patent [19]

Beattie et al.

[11] Patent Number: 5,342,935
[45] Date of Patent: Aug. 30, 1994

[54] ANTAGONISTS OF IMMUNOSUPPRESSIVE MACROLIDES

[75] Inventors: Thomas R. Beattie, Scotch Plains; Matthew J. Wyvratt, Mountainside; Francis J. Dumont, Rahway, all of N.J.

[73] Assignee: Merck & Co., Inc., Rahway, N.J.

[21] Appl. No.: 985,088

[22] Filed: Dec. 2, 1992

Related U.S. Application Data

[60] Division of Ser. No. 766,708, Sep. 26, 1991, Pat. No. 5,190,950, which is a continuation of Ser. No. 551,811, Jun. 25, 1990, abandoned.

[51] Int. Cl.$^5$ .......................................... C07D 267/00
[52] U.S. Cl. ............................................... 540/456
[58] Field of Search ............... 540/456; 514/183, 29.1, 514/411

[56] References Cited

U.S. PATENT DOCUMENTS 4,894,366  1/1990  Okuhara et al. ................. 514/63
4,929,611  5/1990  Okuhara et al. ................. 514/183

FOREIGN PATENT DOCUMENTS 0184162   6/1986  European Pat. Off. .
0315978   5/1989  European Pat. Off. .
0323042   7/1989  European Pat. Off. .
WO89/05304 6/1989 PCT Int'l Appl. .
WO91/04025 4/1991 PCT Int'l Appl. .
8905304   6/1989  World Int. Prop. O. .......... 540/456

OTHER PUBLICATIONS

Tanaka, et al., *J. Am. Chem. Soc.*, 109, 5031–5033 (1987).
March, *Adv. Org. Chem.*, 3d ed., John Wiley & Sons, N.Y., 1985, pp. 627 & 1057.
Petros, et al., *FEBS Lett.*, 308(3), 309–314 (Aug. 1992).

*Primary Examiner*—Mukund J. Shah
*Assistant Examiner*—Y. N. Gupta
*Attorney, Agent, or Firm*—J. Eric Thies; David L. Rose; Joseph F. DiPrima

[57] ABSTRACT

Hydroxymacrolides and derivatives of the general structural Formula I:

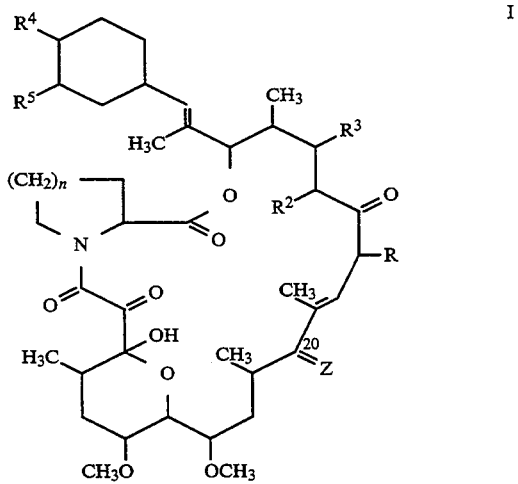

have been prepared from suitable precursors by oxidation at C-20. These macrolides are useful as antagonists of FK-506-type immunosuppressants. The compounds of the present invention are useful for modifying dosages of FK-506-type immunosuppressants in the treatment of autoimmune diseases, infectious diseases and/or the prevention of rejection of foreign organ transplants. In addition, the compounds of the present invention have utility as antidotes for overdoses of FK-506-type immunosuppressants.

2 Claims, No Drawings

ANTAGONISTS OF IMMUNOSUPPRESSIVE MACROLIDES

This is a division of application Ser. No. 07/766,908, filed Sep. 26, 1991, now U.S. Pat. No. 5,190,950, which is a continuation of application Ser. No. 07/551,811, filed Jun. 25, 1990, now abandoned.

SUMMARY OF THE INVENTION

The present invention is related to hydroxymacrolides which are useful in a mammalian host for the modification of treatment of autoimmune diseases (such as juvenile-onset diabetes mellitus, multiple sclerosis and rheumatoid arthritis), infectious diseases and/or the prevention of rejection of foreign organ transplants, e.g. bone marrow and heart transplants with FK-506-type immunosuppressants. In addition, the compounds of the present invention have antagonistic properties to FK-506-type immunosuppressants and so may have utility in the reversal of immunosuppressive activity of FK-506-type immunosuppressive agents.

More particularly, this invention relates to compounds of the general structural Formula I:

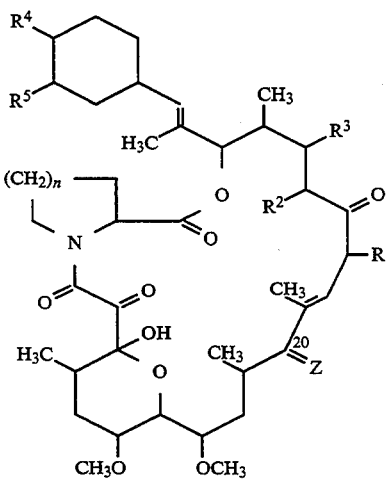

I wherein Z, R, $R^1$, $R^2$, $R^3$, $R^4$, $R^5$ and n are as hereinafter defined.

This invention also relates to pharmaceutical compositions containing the compounds and to a method of use of the present compounds for the modification of the treatment of autoimmune diseases, infectious diseases, the rejection of foreign organ transplants with FK-506-type immunosuppressants and for the treatment of overdoses of FK-506-type immunosuppressants.

BRIEF DESCRIPTION OF DISCLOSURES IN THE ART

Fujisawa United States, European and Japanese patents (U.S. Pat. No. 4,894,366, issued Jan. 16, 1990, EPO Publication No. 0,184,162 and PBJ Disclosure 63-17884) and publications (J. Am. Chem. Soc., 1987, 109, 5031 and J. Antibiotics 1987, 40, 1249) disclose 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (FK-506, FR-900506), 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (FK-520, FR-900520) and related compounds which are the starting materials for the preparation of the compounds described. The synthetic preparation of the aforementioned starting material (FK-506, FR-900506) has recently been reported (J. Am. Chem. Soc., 1989, 111, 1157). A Fisons European patent application (EPO Publication No. 0,323,042) discloses the preparation of various derivatives of FK-506-type immunosuppressants, including 17-allyl-1,14,20-trihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. A Fujisawa United States patent (U.S. Pat. No. 4,929,611, issued May 29, 1990) discloses the use of FK-506-type compounds in treating resistance to transplantation.

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple sclerosis and other disorders such as Chrons disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was licensed by the US FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, FK-506 (FR-900506),

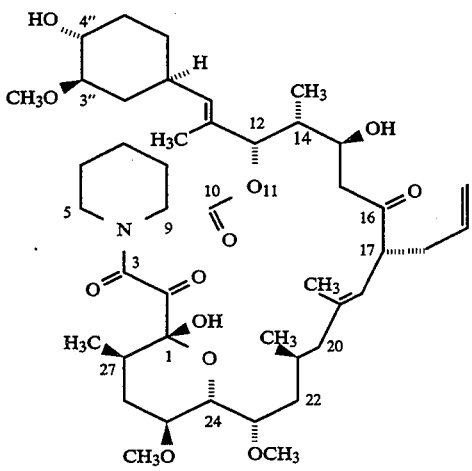

and related compounds which were isolated and characterized by Tanaka, Kuroda, and co-workers at Fujisawa Pharmaceutical Co. in Japan (see *J. Am. Chem. Soc.*, 1987, 109, 5031, and U.S. Pat. No. 4,894,366 (issued Jan. 16, 1990)) have been shown to possess exceptional immunosuppressive activity. A Fujisawa United States patent (U.S. Pat. No. 4,929,611, issued May 29, 1990) discloses the use of FK-506-type compounds in treating resistance to transplantation. In particular, the compound FK-506 (FR-900506) has been reported to be 100 times more effective than cyclosporin in the supression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

A Fisons European patent application (EPO Publication No. 0,323,042) discloses various derivatives of FK-506-type immunosuppressants related to the present application, such as 18-hydroxy FK-506, which are described as having immunosuppressive activity (as determined in Mixed Lymphocyte Reaction Tests and Graft Versus Host Assay). In contrast, the compounds of the present invention are antagonists and have the ability to block the activity of FK-506-type immunosuppressants.

As used herein the term "agonist" denotes ability to initiate or promote a particular drug activity. The term "antagonist" denotes the ability to block a particular drug activity.

Accordingly, an object of the present invention is to provide new analogs of these tricyclomacrolides which will (1) modify the restoration of the balance of the help-and-suppression mechanism of the immune system with macrolide immunosuppressants and (2) modify the induction of transplantation tolerance by macrolide immunosuppressants.

An additional object of the present invention is to provide new analogs of these tricyclomacrolide immunosuppressants which have antagonistic properties. These analogs would find utility in the reversal of the immunosuppressive activity of other FK-506-type immunosuppressive agents and so provide antidotes for overdoses of the immunosuppressants.

An additional object of the present invention is to provide pharmaceutical compositions for administering to a patient one or more of the active macrolide antagonists of the present invention for the modification of treatment with FK-506-type macrolides having immunosuppressive activity.

Still a further object of this invention is to provide a method of modifying the activity of FK-506-type immunosuppressants (which are utilized in controlling graft rejection, autoimmune and chronic inflammatory dieases) by administering a sufficient amount of one or more of the novel macrolide immunosuppressive antagonists in a mammalian species in need of such treatment.

Finally, it is the object of this invention to provide processes for the preparation of the active compounds of the present invention.

DETAILED DESCRIPTION OF THE INVENTION

A. Scope of the Invention

The novel compounds of this invention have structural formula I

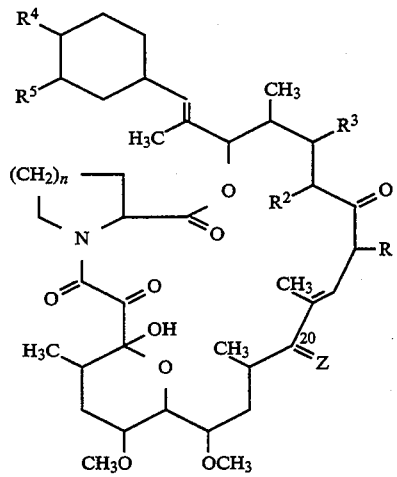

wherein:

Z is ($OR^1$, H) or oxo;

R is methyl, ethyl, propyl or allyl;

$R^1$ is hydrogen, $C_1$–$C_6$ alkanoyl, aryl $C_1$–$C_6$ alkanoyl or aroyl;

$R^2$ is hydrogen, or $R^2$ and $R^3$ taken together form a double bond;

$R^3$ is hydrogen, hydroxy, $C_1$–$C_6$ alkoxy, $C_1$–$C_6$ alkanoyloxy, aryl $C_1$–$C_6$ alkanoyloxy or aroyloxy;

$R^4$ is hydroxy, $C_1$–$C_6$ alkanoyloxy, aryl $C_1$–$C_6$ alkanoyloxy or aroyloxy;

$R^5$ is hydroxy, methoxy, $C_1$–$C_6$ alkanoyloxy, aryl $C_1$–$C_6$ alkanoyloxy or aroyloxy;

n is 1 or 2, with the proviso that when R is allyl and n is 2, $R^1$ is not hydrogen.

The compounds of the present invention have asymmetric centers and this invention includes all of the stereoisomeric pairs such as optical and geometrical isomers and mixtures thereof.

In addition compounds with carbon-carbon double bonds may occur in Z- and E- forms with all isomeric forms of the compounds being included in the present invention.

When any variable (e.g., alkyl, alkanoyloxy, etc.) occurs more than one time in any variable or in Formula I, its definition on each occurrence is independent of its definition at every other occurrence.

As used herein, "alkyl" is intended to include both branched- and straight-chain saturated aliphatic hydrocarbon groups having the specified number of carbon atoms, representative examples being methyl, ethyl, isopropyl, tert-butyl, and sec-butyl; "alkoxy" represents an alkyl group of indicated number of carbon atoms attached through an oxygen bridge. "Alkanoyl" is intended to include those alkylcarbonyl groups of specified number of carbon atoms, which are exemplified by formyl, acetyl, propanoyl and butanoyl; "arylalkanoyl" is intended to include those alkylcarbonyl groups of specified number of carbon atoms bearing an aryl group, which are exemplified by phenylacetyl, phenylpropanoyl and phenylbutanoyl; "alkanoyloxy" is intended to include those alkylcarbonyl groups of an indicated number of carbon atoms attached through an oxygen bridge, which are exemplified by formate, acetate, propionate and butyrate; "arylalkanoyloxy" is intended to include those alkylcarbonyl groups of an indicated number of carbon atoms bearing an aryl group attached through an oxygen bridge, which are exemplified by phenylacetate, phenylpropionate and phenylbutyrate. "Aroyl" is intended to include arylcarbonyl groups, which are exemplified by benzoyl, toluoyl, xyloyl, naphthoyl, nitrobenzoyl, dinitrobenzoyl, nitronaphthoyl, etc; "aryloxy" is intended to include arylcarbonyl groups attached through an oxygen bridge, which are exemplified by benzoyloxy, toluoyloxy, xyloyloxy, naphthoyloxy, nitrobenzoyloxy, dinitrobenzoyloxy, nitronaphthoyloxy, etc;

In the present invention it is preferred that in compounds of Formula I:

Z is (OR$^1$, H) or oxo;
R is methyl, ethyl, propyl or allyl;
R$^1$ is hydrogen or acetyl;
R$^2$ is hydrogen;
R$^3$ is hydrogen, hydroxy or acetoxy;
R$^4$ is hydroxy or acetoxy;
R$^5$ is hydroxy or methoxy;
n is 2 with the proviso that when R is allyl and n is 2, R$^1$ is not hydrogen;

Preferred compounds of the present invention are the compounds identified as follows:

17-Ethyl-1,14,20-trihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14,20-trihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,20-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Methyl-1,14,20-trihydroxy-12-[2'-(4'-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,20-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16,20-pentaone;

14-Acetoxy-17-ethyl-1,20-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

20-Acetoxy-17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; and 17-Ethyl-1,14,20-trihydroxy-12-[2'-(4"-acetoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

B. Preparation of Compounds Within the Scope of the Present Invention

The starting materials for the preparation of the compounds of this invention are represented by Formula II:

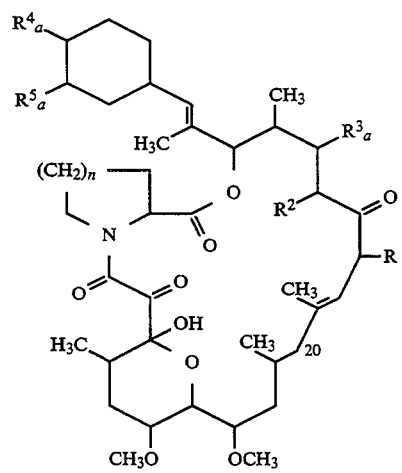

wherein:
R is methyl, ethyl, propyl or allyl;
R$^2$ is hydrogen, or R$^2$ and R$_a^3$ taken together form a double bond;
R$_a^3$ is hydrogen, hydroxy or C$_1$–C$_6$ alkoxy;
R$_a^4$ is hydroxy;
R$_a^5$ is methoxy;
and n is 1 or 2.

The production and characterization of compounds of Formula II is well known in the literature (see U.S. Pat. No. 4,894,366, issued Jan. 16, 1990; EPO Publication No. 0,184,162; EPO Publication No. 0,323,865; PBJ Disclosure 63-17884; *J. Am. Chem. Soc.*, 1987, 109, 5031; and *J. Antibiotics*, 1987, 40, 1249). Both biological fermentation and synthetic processes may be found. A synthetic route to compounds of Formula II can involve modifications of a route described in *J. Am. Chem. Soc.*, 1989, 111, 1157.

Biological fermentation followed by synthetic modification is presently favored in the art as the method to produce compounds of Formula II. Organisms belonging to the genus Streptomyces such as *Streptomyces tsukubaensis*, No. 9993 and *Streptomyces hygroscopicus*, No. 7238 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where R is allyl, $R^2$ is hydrogen, $R^3_a$ and $R^4_a$ are hydroxy, $R^5_a$ is methoxy and n is 2; (B) where R is ethyl, $R^2$ is hydrogen, $R^3_a$ and $R^4_a$ are hydroxy, $R^5_a$ is methoxy and n is 2; (C) where R is methyl, $R^2$ is hydrogen, $R^3_a$ are $R^4_a$ are hydroxy, $R^5_a$ is methoxy and n is 2; and (D) where R is allyl, $R^2$ is hydrogen, $R^3_a$ and $R^4_a$ are hydroxy, $R^5_a$ is methoxy and n is 1.

A lyophilized sample of the isolated *Streptomyces tsukubaensis*, No. 9993 was deposited with the Fermentation Research Institute, Agency of Industrial Science and Technology (No. 1-3, Higashi 1-chome, Yatabemachi Tsukuba-gun, Ibaraki Prefecture, Japan) under the deposit number of FERM P-7886 (deposit date: Oct. 5th, 1985), and then converted to Budapest Treaty route of the same depository on Oct. 19, 1985 under the new deposit number of FERM BP-927.

Using the four compounds produced in the fermentation above, the remaining compounds of Formula II may be easily produced. The allyl of R may be conveniently reduced to propyl by well known methods, for example as disclosed in U.S. Pat. No. 4,894,366. The hydroxy's of $R^3_a$ or $R^4_a$ may be protected by well known methods, for example as disclosed in U.S. Pat. No. 4,894,366. In addition, the hydroxy of $R^3_a$ may be reduced to a hydrogen or eliminated to form a double bond with $R^2$ (by methods disclosed in U.S. Pat. No. 4,894,366 or EPO Publication No. 0,323,042).

The methoxy of $R^5_a$ as produced may be replaced with hydroxy or demethylated and subsequently protected as desired, if necessary. This demethylation of $R^5_a$ may be carried out in a fermentation reaction using the compounds of Formula II as a feedstock. For instance, the compound named under Formula II above wherein R is allyl, $R^2$ is hydrogen, $R^3_a$ is hydroxy, $R^4_a$ is hydroxy, $R^5_a$ is methoxy and n is 2 may be demethylated at $R^5_a$ above using the microorganism Actinoplanacete sp. ATCC No. 53771 (described in EPO Publication No. 0,349,049) or by using the microorganism *Streptomyces tsukubaensis*, No. 9993 (described in EPO Publication No. 0,353,678). Similarly, the compound named under Formula II above wherein R is ethyl, $R^2$ is hydrogen, $R^3_a$ is hydroxy, $R^4_a$ is hydroxy, $R^5_a$ is methoxy and n is 2 may be demethylated at $R^5_a$ above using the microorganism Actinoplanacete sp. ATCC No. 53771 (described in EPO Publication No. 0,349,061). In addition, the compound of Formula II wherein R is ethyl, $R^2$ is hydrogen, $R^3_a$ is hydroxy, $R^4_a$ is hydroxy, $R^5_a$ is hydroxy and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (as described in U.S. Ser. No. 323,653, filed Mar. 15, 1989/EPO Application No. 90,302,669.8, filed Mar. 13, 1990). Similarly, the compound of Formula II wherein R is methyl, $R^2$ is hydrogen, $R^3_a$ is hydroxy, $R^4_a$ is hydroxy, $R^5_a$ is hydroxy and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (as described in U.S. Ser. No. 323,655, filed Mar. 15, 1989/EPO Application No. 90,302,670.6, filed Mar. 13, 1990). The hydroxy of $R^5_a$ may be protected by methods similar to those known for the protection of the hydroxy's of $R^3_a$ and/or $R^4_a$, for example as disclosed in U.S. Pat. No. 4,894,366.

Suitable protecting groups for hydroxyl include those groups well known in the art which are:

1-(lower alkylthio)(lower)alkyl, wherein "lower alkyl" indicates a straight, cyclic or branched chain of one to six carbon atoms, such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, in which the preferred one may be $C_1$-$C_4$ alkylthiomethyl and the most preferred one may be methylthiomethyl; trisubstituted silyl such as tri(lower)alkylsilyl (e.g. trimethylsilyl, triethylsilyl, tributysilyl, tri-i-propylsilyl, t-butyldimethylsilyl, tri-t-butylsilyl, etc.), lower alkyldiarylsilyl (e.g. methyl-diphenylsilyl, ethyl-diphenylsilyl, propyl-diphenylsilyl, t-butyldiphenylsilyl, etc.), and the like, in which the preferred one may be tri($C_1$-$C_4$)alkylsilyl and $C_1$-$C_4$ alkyl-diphenylsilyl, and the most preferred one may be tert-butyl-dimethylsilyl, tri-i-propylsilyl and tert-butyl-diphenylsilyl; acyl such as aliphatic acyl, aromatic acyl and aliphatic acyl substituted with aromatic group, which are derived from carboxylic acids; and the like.

Compounds A, B, C and D of Formula II, organisms to produce the same, conditions of fermentation, separation techniques, and chemical modification of the products are fully described in U.S. Pat. No. 4,894,366, issued Jan. 16, 1990.

The novel processes for preparing the novel compounds of the present invention are illustrated as follows wherein Z, R, $R^1$, $R^2$, $R^3$, $R^4$, $R^5$ and n are as defined above unless otherwise indicated.

REACTION SCHEME A

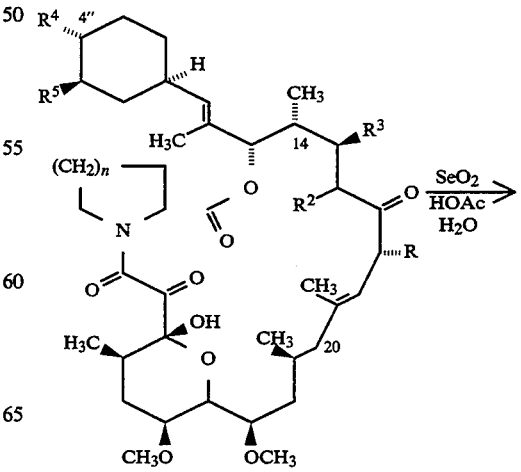

-continued
REACTION SCHEME A
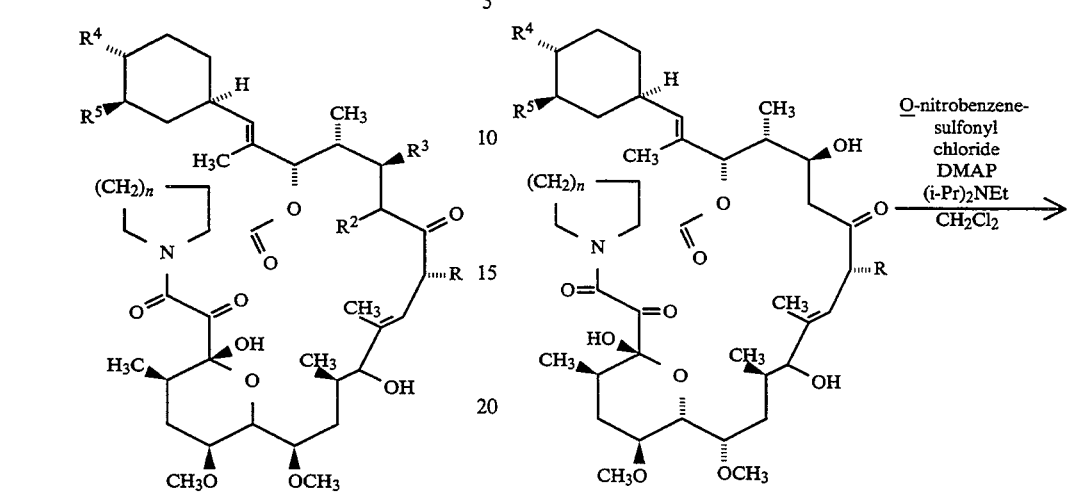
REACTION SCHEME B
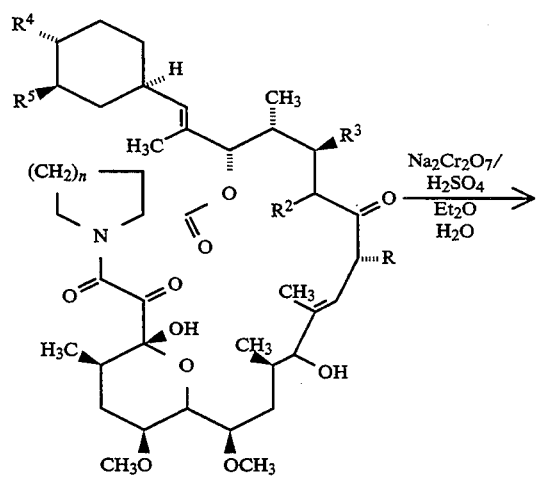
REACTION SCHEME C
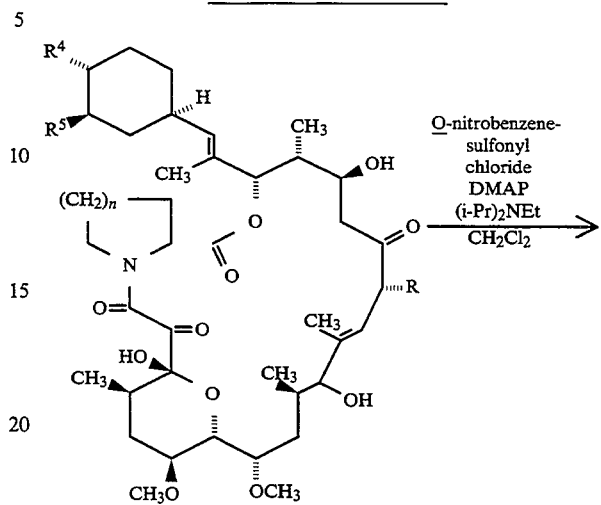
REACTION SCHEME D
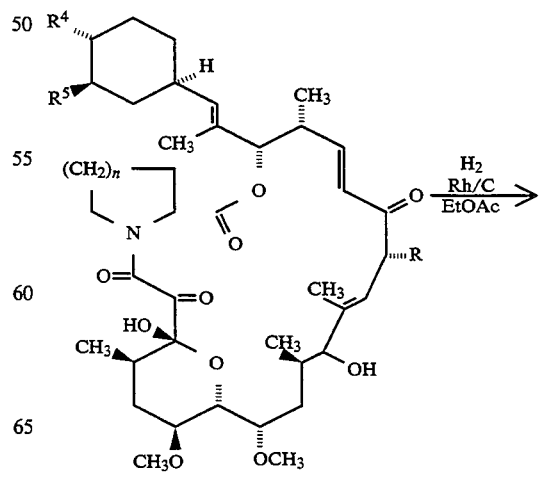

-continued
REACTION SCHEME D

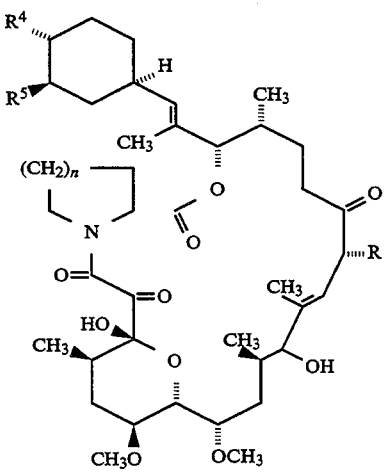

REACTION SCHEME E

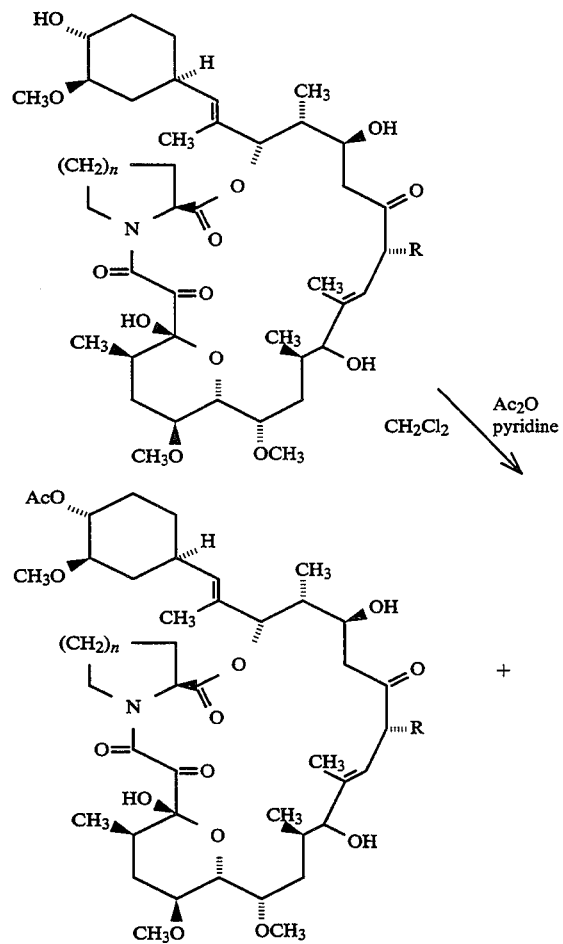

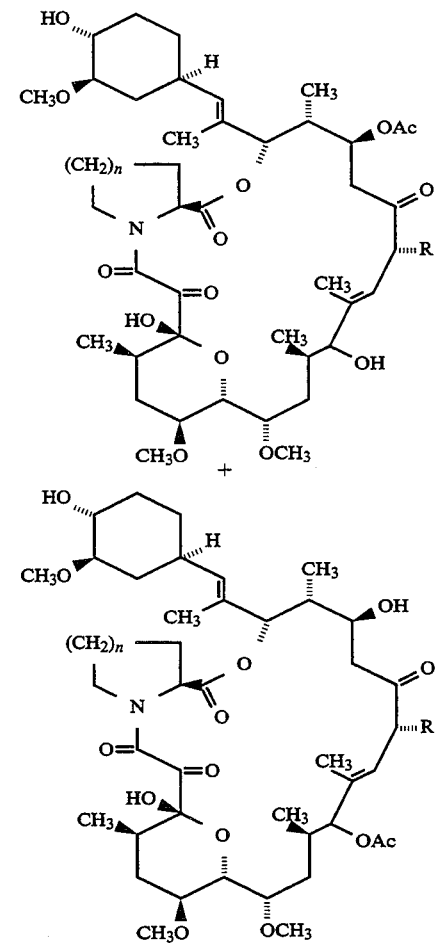

bly ethanol at or near solvent reflux temperature, or with a catalytic amount of selenium dioxide in the presence of an excess of tert-butyl hydroperoxide in a mixture of water and an organic solvent such as methylene chloride or chloroform at or near room temperature. The 20-hydroxy macrolide is predominantly a single isomer at C-20, but a small amount of the epimer at C-20 is also isolated.

The 20-hydroxy macrolide may be oxidized at C-20 as shown in Reaction Scheme B utilizing Brown-Garg reagent (or similar chromate oxidizing agent) in water/diethyl ether to give the ketone at C-20.

The 14,20-dihydroxy macrolide may be modified by elimination of the hydroxy at C-14 to give the corresponding 14,15-dehydro macrolide. As shown in Reaction Scheme C treatment of the 14,20-dihydroxy macrolide with o-nitrobenzenesulfonyl chloride in the presence of 4-dimethylaminopyridine and diisopropylethylamine or triethylamine results in elimination of the hydroxy at C-14 to give the corresponding macrolide bearing an olefin between C-14 and C-15.

As shown in Reaction Scheme A the 20-hydroxy macrolide is prepared by reaction of an appropriate macrolide (wherein $R^2$ is hydrogen, $R^3$ is hydrogen or hydroxy, or $R^2$ and $R^3$ taken together form a double bond, $R^4$ is hydroxy, and $R^5$ is hydroxy or methoxy) with selenium dioxide in glacial acetic acid and water at our near room temperature, with selenium dioxide in the presence of an amine base, such as pyridine in a protic solvent such as a lower alkanoyl solvent, prefera- As shown in Reaction Scheme D the 14,15-dehydro-20-hydroxy macrolide is reduced under an atmosphere of hydrogen in the presence of a noble metal catalyst, such as rhodium on carbon catalyst or rhodium on alumina catalyst, at a pressure of atmospheric pressure to 40 psig, at or near room temperature in an organic solvent such as ethyl acetate or ethanol for about 1 to 24 hours, or until the requisite amount of hydrogen is absorbed to reduce the 14,15-olefin and give the 14-deoxy-20-dihydroxymacrolide of Formula I.

As illustrated in Reaction Scheme E, hydroxy macrolides may be acylated by reaction with an acid halide of formula $C_1$–$C_6$ alkanoyl halide, aryl $C_1$–$C_6$ alkanoyl halide, or aroyl halide or with an acid anhydride of formula ($C_1$–$C_6$ alkanoyl)$_2$O, (aryl $C_1$–$C_6$ alkanoyl)$_2$O, or (aroyl)$_2$O, in the presence of an amine base in a suitable inert, non-protic, organic solvent at a temperature between 0° C. and 50° C. for a sufficient time to form the acrylated derivatives. Treatment of the 4″,14,20-trihydroxy macrolide with acetic anhydride in the presence of pyridine gives a mixture of the corresponding macrolides bearing an acetate functionality at C-4″, C-14 and/or C-20. Similarly, treatment of the 3″,4″,14,20-tetrahydroxy macrolide with acetic anhydride in the presence of pyridine gives a mixture of the corresponding macrolides bearing an acetate functionality at C-3″, C-4″, C-14 and/or C-20.

The object compounds of Formula I obtained according to the reactions as explained above can be isolated and purified in a conventional manner, for example, extraction, precipitation, fractional crystallization, recrystallization, chromatography, and the like.

It is to be noted that in the aforementioned reactions and the post-treatment of the reaction mixture therein, the stereo isomer(s) of starting and object compounds due to asymmetric carbon atom(s) or double bond(s) of the object compounds of Formula I may occasionally be transformed into the other stereo isomer(s), and such cases are also included within the scope of the present invention.

In the present invention, compounds with asymmetric centers may occur as racemates, racemic mixtures and as individual diastereomers, with all isomeric forms of the compounds being included in the present invention. These may be prepared by methods such as those disclosed in publications which describe synthetic routes to fragments of the macrolide FK-506 (FR-900506) and the total synthesis of the macrolide FK-506 (FR-900506) itself (*Tetrahedron Lett.*, 1988, 29, 277; *Tetrahedron Lett.*, 1988, 29, 281; *Tetrahedron Lett.*, 1988, 29, 4481; *J. Org. Chem.*, 1989, 54, 9; *J. Org. Chem.*, 1989, 54, 11; *J. Org. Chem.*, 1989, 54, 15; *J. Org. Chem.*, 1989, 54, 17; *J. Am. Chem. Soc.*, 1989, 111, 1157).

C. Utility of the compounds within the scope of the invention

The compounds of Formula I may be employed as antagonists of FK-506-type immunosuppressants by methods and in dosages known in the prior art for compounds of Formula II. These compounds possess pharmacological activity such as antagonism of immunosuppressive activity, and the like, and therefore are useful for the modification of the treatment of the resistance to transplantation or transplantation rejection of organs or tissues such as heart, kidney, liver, medulla ossium, skin, etc., graft-versus-host diseases by medulla ossium transplantation, autoimmune diseases such as rheumatoid arthritis, systemic lupus erythematosis, Hashimoto's thyroiditis, multiple sclerosis, myasthenia gravis, type I diabetes, uveitis, etc., by FK-506-type immunosuppressants. In addition, the compounds of Formula I have antagonistic properties and so may have utility in the reversal of immunosuppressive activity of other FK-506-type immunosuppressive agents.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semi-solid, or liquid form, and in addition auxiliary, stabilizing, thickening and coloring agents and perfumes may be used. The active object compound is included in the pharmaceutical composition in an amount sufficient to produce the desired effect upon the process or condition of diseases.

This invention also relates to a method for the modification of the treatment of patients suffering from immunoregulatory abnormalities involving the administration of a compound of Formula I as the active constituent.

For the modification of the treatment with FK-506-type immunosuppressants of these conditions and diseases caused by immmunoirregularity a compound of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. For applying a composition of this invention to a human, it is preferable to apply it by parenteral or oral administration.

Dosage levels of the compounds of the present invention of the order from about 0.01 mg to about 50 mg per kilogram of body weight per day, preferably from about 0.1 mg to about 10 mg per kiolgram body weight per day, are useful in the treatment of the above-indicated conditions (from about 0.7 mg to about 3.5 gm per patient per day, assuming a 70 kg patient). In addition, the compounds of the present invention may be administered on an intermittent basis; i.e. at semiweekly, weekly, semimonthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 1 gm of active agent compounded with an appropriate and convenient amount of carrier material which may vary from about 5 to about 95 percent of the total composition. Dosage unit forms will generally contain from about 0.5 mg to about 500 mg of active ingredient. For topical administration in larger mammals a preparation containing a 1–3% concentration of active agent may be utilized.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE 1

17-Ethyl-1,14,20-trihydroxy-12-[2''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 6 g (7.59 mmole) of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (containing approximately 10% of the 17-methyl analog) and 0.87 g (7.84 mmole) selenium dioxide in 60 ml glacial acetic acid and 10 ml water was stirred at 22° C. for 21 hours. The solution was lyophilized and the residue was chromatographed on 300 g silica gel using methylene chloride and methanol/methylene chloride as eluent. The new product was rechromatographed on silica gel with 4% methanol/methylene chloride as eluent to yield 1.68 g (27% yield) 17-ethyl-1,14,20-trihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

$^1$HNMR (CDCl$_3$) (selected signals) δ: 4.12 (broad singlet, 1H, H$_{20}$), 5.65, (doublet, J=9.5 Hz, 1H, H$_{18}$).

Mass spectra: m/e at 807, 789, 771, 580, 562,

Analysis: Calculated for C$_{43}$H$_{69}$NO$_{13}$: C, 63.92; H, 8.61; N, 1.73. Found: C, 64.24; H, 8.92; N. 1.76.

A small amount of a compound epimeric at C-20 was isolated from the crude product by chromatography on silica gel using ethyl acetate as eluent, wherein the minor epimer moves slower than the major epimer.

$^1$HNMR (CDCl$_3$) (selected signals) δ: 4.08 (broad singlet, 1H, H$_{20}$), 5.48 (doublet, J=9.5 Hz, 1H, H$_{18}$).

Mass spectrum: m/e at 807 (weak), 789, 771, 580, 562.

EXAMPLE 2

17-Ethyl-1,20-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (Alternate Method)

To a solution of 17-ethyl-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (735 mg) in 95% ethanol (10 ml) was added 130 mg of selenium dioxide. The flask was fitted with a water condenser and heated to 70° C. on a mantle. After 45 hours the mixture was cooled to room temperature, filtered through diatomaceous earth and the filtrate poured into a saturated sodium bicarbonate solution. This was extracted with ethyl acetate, and the organic phase was washed with brine and dried over magnesium sulfate. The solution was concentrated and purified by flash chromatography on silica gel (ethyl acetate:hexane (1:1)+1% methanol) to give the title compound (514 mg).

$^1$HNMR (CDCl$_3$) (selected signals) δ: 5.49 (brd J=10 Hz, 1H); 5.22 (brd J=10 Hz, 1H)); 4.69 (major), 4.36 (minor) (brs, 1H); 3.84 (d J=8.3 Hz, 1H); 2.81 (d J=4 Hz, 1H); 2.63 (brs, 1H).

Mass spectra: m/e at 814 (M+Na).

EXAMPLE 3

17-Methyl-1,14,20-trihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A homolog characterized by the presence of a 17-methyl substituent in place of the 17-ethyl substituent was isolated by high pressure liquid chromatography from the crude product of Example 1. Two samples of 97 mg and 100 mg were injected into a Whatman Magnum 20 Partisil 10 ODS-3 column. Using 55% acetonitrile/45% water at a flow of 6 ml/min an early peak of 21.9 mg was collected. Reinjection and collection under the same conditions provided 13.4 mg of a new compound identified as 17-methyl-1,14,20-trihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

$^1$HNMR (CDCl$_3$) (selected signals) δ: 1.15 and 1.22 (pair of doublets in ratio of 3:2, J=6.5 Hz, 17-CH$_3$), 4.08 (broad singlet, 1H, H$_{20}$), 5.67 and 5.27 (pair of doublets in ratio of 3:2, J=9.5 Hz, H$_{18}$).

Mass spectrum: m/e at 793, 775, 757, 566, 548.

EXAMPLE 4

17-Ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16,20-pentaone To 494.3 mg (0.6125 mmole) of 17-ethyl-1,14,20-trihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in 20 ml ethyl ether stirred at 22° C. was added 0.45 ml of Brown-Garg reagent (prepared from 5.0 g of sodium dichromate dihydrate and 3.75 ml. of conc. sulfuric acid diluted to 25 ml with water) in 3 increments of 0.15 ml at times of 0, 30 and 85 minutes. At 80 minutes stirring after the last addition the ether layer was decanted. The aqueous layer was washed well with ether, which was added to the ether decantate. Evaporation of the ether layer led to a crude residue which was purified first by preparative thin layer chromatography on silica gel using 5% methanol in methylene chloride as eluent and then by similar purification using ethyl acetate as eluent. The product, 53.6 mg, was identified as 17-ethyl-1,14-di-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16,20-pentaone.

$^1$HNMR (CDCl$_3$) (selected signals) δ: 6.72 and 6.89 (pair of doublets in ratio of 2:1, J=9.5 Hz, 1H, H$_{20}$).

Mass spectrum: m/e at 805, 787, 769, 578.

EXAMPLE 5

17-Ethyl-1,20-dihydroxy-12-[2'-(4''-hydroxy-3''-methoxycyclohexyl)-1'-methylvinyl]23,25-dimethoxy-13,19,21,27-tetramethyl-11,28-dioxa-4-azatricyclo[22.3.1.0$^{4,9}$]octacos-14,18-diene-2,3,10,16-tetraone To a solution of 404.5 mg of 17-ethyl-1,14,20-trihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, 64.8 mg 4-dimethylaminopyridine, 87.1 μl of diisopropyl ethyl amine and 4 ml methylene chloride stirred magnetically at 0° C. was added 113.2 mg o-nitrophenylsulfonyl chloride in 2 ml methylene chloride. At 19 hours the mixture was evaporated and purified by thin layer chromatography on silica gel using hexane/acetone mixtures (60/40 and 50/50) as eluent. The faster moving compound, 155 mg, was repurified on silica gel preparative thin layer chromatography using ethyl acetate as eluent. The slower moving compound, 69.8 mg, was identified as 17-ethyl-1,2-0-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone.

$^1$HNMR (CDCl$_3$) (selected signals) δ: 5.56 and 6.64 (pair of doublets, 1H, H$_{18}$), 6.15 (2 double doublets (8 lines), 1H, H$_{15}$), 6.80 (overlapping double doublets, 1H, H$_{14}$).

Mass spectrum: m/e 789, 771, 753, 602.

EXAMPLE 6

17-Ethyl-1,20-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone
(Alternate Method)

To a stirred solution of 17-ethyl-1,14,20-trihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (in benzene) is added p-toluenesulfonic acid and the mixture warmed to 60° C. in an oil bath. The reaction mixture is cooled to room temperature, neutralized by the addition of a saturated aqueous NaHCO$_3$ solution and extracted with ethyl acetate (3 times). The combined organics are washed with saturated NaCl solution, dried over Na$_2$SO$_4$ and purified by flash chromatography on silica gel (20% hexanes in ethyl acetate and 1% MeOH) to yield the title compound.

EXAMPLE 7

17-Ethyl-1,20-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone A solution of 17-ethyl-1,20-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone in ethyl acetate is hydrogenated at 40 p.s.i. in a shaker apparatus using hydrogen and 5% rhodium on carbon catalyst until one molar equivalent of hydrogen is consumed. Filtration to remove catalyst and evaporation to remove solvent affords the product reduced at the Δ$^{14,15}$-position.

EXAMPLE 8

14-Acetoxy-17-ethyl-1,20-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone,
20-Acetoxy-17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, and
17-Ethyl-1,14,20-trihydroxy-12-[2'-(4''-acetoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To 401.9 mg of 17-ethyl-1,14,20-trihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone dissolved in 2 ml of methylene chloride stirred at 22° C. was added 100 μl pyridine and 50 μl acetic anhydride. After 4 days the sample was evaporated and purified by preparative thin layer chromatography using 5% methanol in methylene chloride. The crude product, 183 mg, was further purified by preparative high pressure liquid chromatography using an eluent of 65% acetonitrile/35% water. Individual collected components were identified by NMR and mass spectra.

A. 14-Acetoxy-17-ethyl-1,20-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, 38.9 mg.

$^1$HNMR (CDCl$_3$) (selected signals) δ: 2.00 and 2.04 (singlets in ratio 2:1, 3H, CH$_3$COO), 4.12 (broad singlet 1H, H$_{20}$), 4.65 and 4.72 (broad multiplets in ratio 2:1, 1H, H$_{14}$).

Mass spectrum: m/e 789, 771, 753, 602, 584.

B. 20-Acetoxy-17-ethyl-1,14-dihydroxy-12-[2'-(4''-hydroxy-3''-methoxycyclohexyl)-1'-methyl-vinyl]-23,25-dimethoxy-13,19,21,27-tetramethyl-11,28-dioxa-4-azatricyclo[22.3.1.0$^{4,9}$]octacos-18-ene-2,3,10,16-tetraone, 47.5 mg.

$^1$HNMR (CDCl$_3$) (selected signals) δ: 2.04 and 2.09 (singlets in ratio 2:1, 3H, CH$_3$COO), 3.91 and 3.98 (broad multiplets in ratio 2:1, 1H, H$_{14}$), 5.23 (broad singlet, 1H, H$_{20}$), 5.40 (doublet, 1H, H$_{18}$).

Mass spectrum: m/e 849, 789, 771, 753, 602.

C. 17-Ethyl-1,14,20-trihydroxy-12-[2'-(4''-acetoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, 31.5 mg.

NMR (CDCl$_3$) (selected signals) δ: 2.08 (singlet, 3H, CH$_3$COO), 4.12 (broad multiplet, 1H, H$_{20}$), 3.66 and 3.69 (2 multiplets, 1H, H$_4$''), 5.65 (doublet, 1H, H$_{18}$).

Mass spectrum: m/e 849, 831, 813, 795, 580, 562.

EXAMPLE 9

17-Ethyl-1,14,20-trihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound is prepared by the method of Example 1 utilizing 17-ethyl-1,14-dihydroxy-12-[2'-(3''

,4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone as starting material.

EXAMPLE 10

14-Acetoxy-17-ethyl-1,20-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone,
20-Acetoxy-17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone,
17-Ethyl-1,14,20-trihydroxy-12-[2'-(4''-acetoxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, and
17-Ethyl-1,14,20-trihydroxy-12-[2'-(3''-acetoxy-4''-hydroxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compounds are prepared by the method of Example 8 utilizing 17-ethyl-1,14,20-trihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone as starting material.

EXAMPLE 11

Antagonism Assay
1. Sample Preparation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^{-5}$M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The various dilutions of the compound to be tested were then added in triplicate wells at 20 μl/well. For antagonist activity, dilutions of compounds were cultured with 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (as a standard) at a concentration of 1.2 nM, a concentration which inhibits T cell proliferation by 100%. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Camgridge, MA). After another 4 hours of incubation, cultures were harvested on glass fiber filters using a multiple sample harvester. Radioactivity of filter discs corresponding to individual wells was measured by standard liquid scintillation counting methods (Beta-counter). Mean counts per minute of replicate wells were calculated and the results expressed as concentration of compound required to inhibit tritiated thymidine uptake of T-cells by 50%.

A selection of compounds were tested according to the previous procedure. The concentration of compound required to reverse the inhibition obtained by 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (the standard) alone, by 50% was measured, and the results were as follows:

| Example No. Of Product Compound | $ED_{50}(M)$ |
|---|---|
| 1 | $<5 \times 10^{-5}$ |
| 4 | $<5 \times 10^{-5}$ |
| 5 | $<5 \times 10^{-5}$ |
| 8A | $<5 \times 10^{-5}$ |
| 8B | $<5 \times 10^{-5}$ |
| 8C | $<5 \times 10^{-5}$ |

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound which is: 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16,20-pentaone.

2. The compound of claim 4 which is:

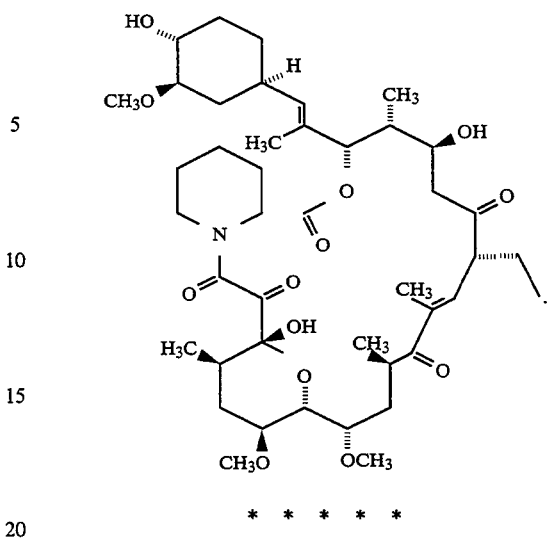
* * * * *